United States Patent
Efremkin

(10) Patent No.: US 11,433,254 B2
(45) Date of Patent: *Sep. 6, 2022

(54) APPARATUS AND METHOD FOR TREATMENT OF WOUNDS AND SKIN MEDICAL CONDITIONS AT A PREDETERMINED SKIN AREA

(71) Applicant: Pavel V. Efremkin, Ardsley, NY (US)

(72) Inventor: Pavel V. Efremkin, Ardsley, NY (US)

(*) Notice: Subject to any disclaimer, the term of this patent is extended or adjusted under 35 U.S.C. 154(b) by 285 days.

This patent is subject to a terminal disclaimer.

(21) Appl. No.: 16/741,715

(22) Filed: Jan. 13, 2020

(65) Prior Publication Data

US 2020/0147407 A1 May 14, 2020

Related U.S. Application Data

(60) Continuation-in-part of application No. 15/635,342, filed on Jun. 28, 2017, now Pat. No. 10,532,219, (Continued)

(51) Int. Cl.
*A61N 5/06* (2006.01)
*A61N 1/40* (2006.01)
(Continued)

(52) U.S. Cl.
CPC .............. *A61N 5/062* (2013.01); *A61B 90/36* (2016.02); *A61F 7/0085* (2013.01);
(Continued)

(58) Field of Classification Search
None
See application file for complete search history.

(56) References Cited

U.S. PATENT DOCUMENTS 5,653,706 A * 8/1997 Zavislan .............. A61B 18/203
606/17
5,735,276 A * 4/1998 Lemelson .............. A61B 18/20
600/407
(Continued)

OTHER PUBLICATIONS

Office Action dated Mar. 25, 2019 for parent U.S. Appl. No. 15/635,342, filed Jun. 28, 2017.
(Continued)

*Primary Examiner* — Carl H Layno
*Assistant Examiner* — Manolis Pahakis
(74) *Attorney, Agent, or Firm* — Lawrence G. Fridman, Esq; Feigin & Fridman, LLC

(57) ABSTRACT

A system for treatment of wounds consists of a treatment housing, a fluid delivery mechanism for supplying debridement fluids to the wound treatment area, an evacuation mechanism for evacuation of debris from the treatment chamber. A handheld device is connected to the treatment housing, wherein its interior accommodates a laser source, a scanning device, an image recording device and at least one sensor/detector, a control unit having a microprocessor for controlling operation of the system. The sensor detects concentration of various substances in the wound, and the microprocessor analyzes data obtained by the sensor and generates signals to adjust parameters of the laser, the liquid dispensing nozzles and the suction outlet to optimize removal of necrotic tissue so as to ultimately to promote wound healing.

17 Claims, 11 Drawing Sheets

Related U.S. Application Data which is a division of application No. 15/168,896, filed on May 31, 2016, now Pat. No. 9,694,200, which is a division of application No. 14/216,995, filed on Mar. 17, 2014, now Pat. No. 9,375,586.

(60) Provisional application No. 61/799,896, filed on Mar. 15, 2013.

(51) Int. Cl.

| | | |
|---|---|---|
| *A61M 37/00* | (2006.01) | |
| *A61M 35/00* | (2006.01) | |
| *A61K 33/14* | (2006.01) | |
| *A61K 31/5375* | (2006.01) | |
| *A61F 7/00* | (2006.01) | |
| *A61H 35/00* | (2006.01) | |
| *A61N 5/02* | (2006.01) | |
| *A61B 90/00* | (2016.01) | |
| *A61B 18/00* | (2006.01) | |
| *A61N 5/067* | (2006.01) | |

(52) U.S. Cl.
CPC ....... *A61H 35/006* (2013.01); *A61K 31/5375* (2013.01); *A61K 33/14* (2013.01); *A61M 35/00* (2013.01); *A61M 37/0092* (2013.01); *A61N 1/40* (2013.01); *A61N 5/022* (2013.01); *A61N 5/0616* (2013.01); *A61N 5/0624* (2013.01); *A61B 2018/00452* (2013.01); *A61F 2007/0045* (2013.01); *A61F 2007/0046* (2013.01); *A61M 2037/0007* (2013.01); *A61M 2202/0468* (2013.01); *A61M 2230/005* (2013.01); *A61N 5/067* (2021.08); *A61N 2005/0626* (2013.01); *A61N 2005/0645* (2013.01); *A61N 2005/0652* (2013.01); *A61N 2005/0654* (2013.01); *A61N 2005/0659* (2013.01); *A61N 2005/0661* (2013.01)

(56) References Cited

U.S. PATENT DOCUMENTS

| | | | | |
|---|---|---|---|---|
| 6,293,940 B1* | 9/2001 | Slatkine | A61B 18/20 | 606/17 |
| 6,436,127 B1* | 8/2002 | Anderson | A61B 5/0071 | 128/898 |
| 6,533,774 B1* | 3/2003 | Ota | A61B 18/203 | 607/91 |
| 6,718,196 B1* | 4/2004 | Mah | A61B 8/4218 | 600/117 |
| 7,101,365 B1* | 9/2006 | Sharon | A61B 18/203 | 606/9 |
| 7,201,766 B2* | 4/2007 | Butler | A61N 5/0613 | 607/90 |
| 7,282,060 B2* | 10/2007 | DeBenedictis | A61B 18/203 | 606/9 |
| 7,762,965 B2* | 7/2010 | Slatkine | A61B 18/203 | 601/7 |
| 7,922,751 B2* | 4/2011 | Shanks | A61N 5/0617 | 606/9 |
| 8,475,507 B2* | 7/2013 | Dewey | A61B 18/203 | 607/89 |
| 8,523,849 B2* | 9/2013 | Liu | A61N 5/0613 | 606/9 |
| 8,529,560 B2* | 9/2013 | Ferren | A61B 18/203 | 606/2 |
| 8,784,406 B2* | 7/2014 | Rathjen | A61F 9/00836 | 606/4 |
| 8,784,407 B2* | 7/2014 | Spikker | A61B 18/203 | 606/9 |
| 9,198,735 B2* | 12/2015 | Taghizadeh | A61B 18/14 | |
| 9,364,684 B2* | 6/2016 | Poran | A61B 18/203 | |
| 9,375,586 B2* | 6/2016 | Efremkin | A61N 5/062 | |
| 9,694,200 B2* | 7/2017 | Efremkin | A61K 33/14 | |
| 10,420,608 B2* | 9/2019 | Miao | A61B 5/015 | |
| 10,532,219 B2* | 1/2020 | Efremkin | A61N 5/0616 | |
| 10,945,792 B2* | 3/2021 | Karni | A61B 18/203 | |
| 2001/0053907 A1* | 12/2001 | Ota | A61B 18/203 | 606/17 |
| 2002/0049432 A1* | 4/2002 | Mukai | A61B 18/203 | 606/9 |
| 2005/0154382 A1* | 7/2005 | Altshuler | A61B 18/203 | 606/9 |
| 2006/0200115 A1* | 9/2006 | Ferren | A61B 18/203 | 606/9 |
| 2006/0253176 A1* | 11/2006 | Caruso | A61B 18/203 | 607/88 |
| 2006/0259102 A1* | 11/2006 | Slatkine | A61B 17/205 | 607/88 |
| 2007/0049996 A1* | 3/2007 | Black | A61B 18/203 | 607/89 |
| 2009/0131921 A1* | 5/2009 | Kurtz | A61F 9/00825 | 606/4 |
| 2013/0165821 A1* | 6/2013 | Freedman | A61F 13/0216 | 604/20 |
| 2013/0184693 A1* | 7/2013 | Neev | A61N 5/0617 | 606/9 |
| 2013/0345685 A1* | 12/2013 | Poran | A61N 5/0616 | 606/9 |
| 2015/0230863 A1* | 8/2015 | Youngquist | A61B 18/203 | 606/9 |
| 2017/0361123 A1* | 12/2017 | Efremkin | A61H 35/006 | |
| 2020/0147407 A1* | 5/2020 | Efremkin | A61N 5/022 | |

OTHER PUBLICATIONS

List of References for parent U.S. Appl. No. 15/635,342, filed Mar. 25, 2019.

List of References for parent U.S. Appl. No. 15/635,342, filed Sep. 11, 2019.

* cited by examiner

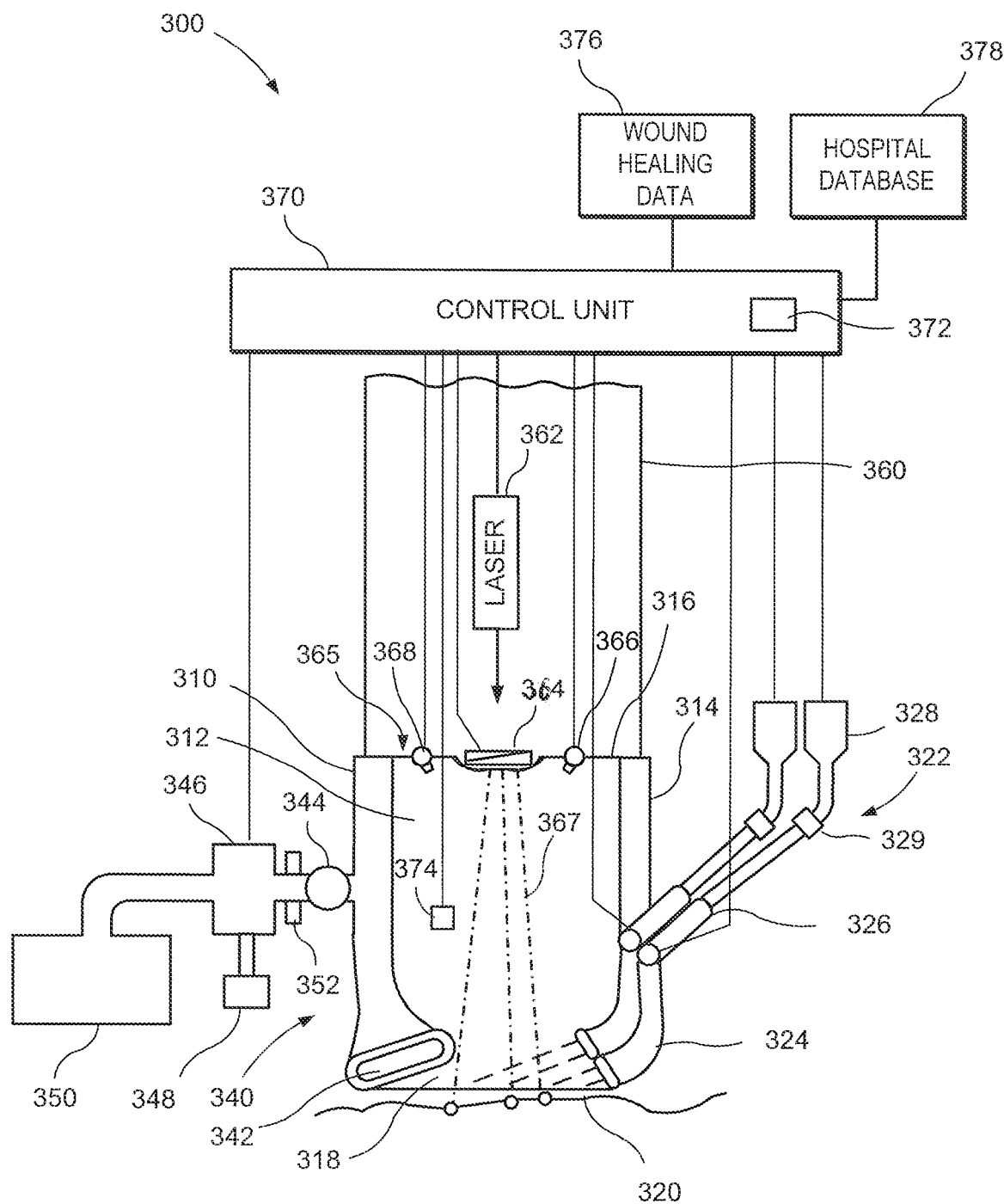
F I G. 7

APPARATUS AND METHOD FOR TREATMENT OF WOUNDS AND SKIN MEDICAL CONDITIONS AT A PREDETERMINED SKIN AREA

REFERENCE TO RELATED APPLICATIONS

This is a Continuation-in-Part Application of Application Ser. No. 15/635,342 filed Jun. 28, 2017, which issued as U.S. Pat. No. 10,532,219, which is a Divisional of U.S. application Ser. No. 15/168,896 filed May 31, 2016, which issued as U.S. Pat. No. 9,694,200, which is a Divisional of U.S. application Ser. No. 14/216,995 filed Mar. 17, 2014, which issued as U.S. Pat. No. 9,375,586, which claims benefit of Provisional Application Ser. No. 61/799,896 filed Mar. 15, 2013, wherein all above applications are incorporated herein by reference in their entirety.

FIELD OF THE INVENTION

This invention relates to wound care devices and a method of treating such wounds.

BACKGROUND OF THE INVENTION

Wound care is a major clinical challenge. Healing and chronic non-healing wounds are associated with a number of biological tissue changes and, a common major concern, bacterial infection. A proportion of wound infections are not clinically apparent and contribute to the growing economic burden associated with wound care. Currently, wound assessment protocols include direct visual inspection of the wound with collection of bacterial swabs and tissue biopsies resulting in delayed, costly and often insensitive bacteriological results. This may affect the timing and effectiveness of treatment. Such visual assessment only provides a superficial view of the wound site but does not provide formation about underlying biological changes that are occurring at the tissue level. A relatively simple apparatus and method based on review of biological information is desirable in clinical wound management.

Mechanism of Wound Healing Description:
   debridement of the wound to remove necrotic tissue, infection and bacteria
   collagen regrowth to regenerate skin tissue
   Suction to evacuate necrotic—or dead tissue from the interior of the treatment chamber formed in the housing.

Debridement involves the removal of necrotic tissue to promote wound healing. During wound healing process, the affected area can become overrun with necrotic or dead tissue. This can be harmful to the body's ability to recover and develop new skin, so debridement may be necessary to remove that dead material.

Debridement promotes the wound healing process in a variety of ways. Not only does dead skin inhibit the development of healthy new tissue, but it makes the affected area more susceptible to infection. It can also hide the signs of infection, as dead tissue can increase odor and exudate, making it easier for bacteria and other harmful foreign invaders to spread.

There are two different categories of debridement: active and autolytic. Autolytic debridement involves application of hydrocolloids and hydrogels to enhance moisture in the affected area in order to degrade it so the body will naturally deslough the dead tissue. Active debridement involves the manual removal of necrotic material, and it comes in several types of procedures, such as:

Surgical debridement: During this operation, a clinician will completely remove the necrotic material using scalpel and forceps, resulting in a bleeding wound bed.

Sharp debridement: This is similar to surgical debridement, except that it involves the use of surgical scissors.

Chemical debridement can be facilitated by applying topical agents that disrupt or digest extracellular proteins. For example, the enzyme collagenase, derived from the fermentation of Clostridium histolyticum, has the unique ability to digest collagen in necrotic tissue. Papain, the proteolytic enzyme from the fruit of carica papaya, is a potent digestant of non-viable protein matter. When combined with urea, studies have shown it has twice as much digestive activity.

A typical prior art method of debridement uses a mechanical instrument—scalpel or blade—to physically remove or scrape the infected top layers of wound tissue. This also leads to removal of newly formed layer of new cell growth on the top surface of the wound that occurred through a natural wound healing process. Thus, the wound is reopened by medical practitioner scraping the top surface of the wound. This often results in chronic wound condition, so that the wound will not close and stay unhealed, open over long period of times especially when multiple debridement sessions are used.

Laser irradiation with optimal parameters is known to kill bacteria, microbes or otherwise disinfect the wound, and to promote collagen growth in the skin tissue.

One of the essential aspects of the invention relates to utilization of the laser energy as an effective tool in wound treatment in general, and more specifically to debridement of the wound as well as accelerating the healing process and closing of the wound. Laser energy with optimally selected parameters including wavelength, energy level, pulse duration, and others can selectively destroy bacteria or microbe affected materials on or within the wound without damaging the healthy cell structure or skin tissue of the wound. Such minimally invasive approach creates a condition for accelerated wound closing by allowing newly grown cells in wound healing process to build up. These results are difficult to achieve with standard_prior art debridement protocol of scraping the infected material from the top surface of the wound by sharp surgical tools which also inevitably resulted in scraping a part of healthy new grown regenerated tissue cells layers. This prior art protocols are known for constantly disturbing the wound and thus ultimately resulted in self feeding circle of chronic wounds.

It has been long felt and unsolved need for a robust, cost-effective, non-invasive and rapid imaging-based method and device for objectively assessing wounds for rapidly and non-invasively detecting the earliest presence of bacteria/microorganisms within wounds. There is also a need for a device that is compact and capable of real-time non-invasive and/or non-contact review of wounds in a safe and convenient manner, and user friendly to the clinician, nurse and wound specialist.

SUMMARY OF THE INVENTION

One aspect of the invention provides system for treatment of wounds. The system includes a treatment housing with a treatment chamber formed in its interior. A fluid delivery mechanism for supplying debridement liquids/fluids the wound treatment includes a nozzle. An evacuation mechanism for evacuation of debris from the treatment chamber is provided with a suction outlet. A handheld device is releasably connected to the top region of the treatment housing and accommodates a laser source, a scanning device, an image recording device and at least one sensors/detectors; a control unit having a microprocessor for controlling operation of the system.

As to another aspect of the invention the sensors detect concentration of various substances in the wound. The microprocessor analyzes data obtained by the sensors and generates signals to adjust parameters of the laser. The liquid dispensing nozzles and the suction outlet to optimize removal of necrotic tissue so as to ultimately to promote wound healing. An algorithm of the microprocessor utilizes wound images generated by the imaging apparatus to define an area to be treated by the laser and guide a laser beam scanning mechanism to thoroughly cover the wound area in an optimal pattern.

As to a further aspect of the invention an automated method for treatment of wounds and skin medical conditions is carried out by means of a system including a treatment vessel disposed at a wound treatment area. A fluid delivery mechanism for supplying debridement fluids to the wound treatment area has at least one nozzle. An evacuation mechanism for evacuation of debris from the treatment chamber is formed having at least one suction outlet. the nozzle and said suction outlet are situated in the treatment chamber at the wound treatment area. A control unit having a microprocessor forms a part of the system. A handheld device is releasably connected to the treatment vessel. An interior of the handheld device accommodates a laser source, a scanning device, an image recording device and at least one sensor/detector.

Essential steps of the method include entering patient identifier data into a wound healing data base to access the memory containing prior patient history and selecting the treatment device/vessel to accommodate specific wound characteristics for optimal treatment of a specific wound at a predetermined skin area.

A wound treatment assembly is formed by connecting the selected treatment device to the fluid delivery mechanism and the evacuation system and attaching the treatment device to the handheld device. Then, the wound treatment vessel of the treatment assembly is positioned on a skin of a patient surrounding the wound. activating the image recording device and the sensors to record and identify various characteristic of the wound.

The data generated by the image generating device and the sensors is transferred to the microprocessor of the control unit, so as to compare the data to the prior patient data stored in the memory to calculate laser parameters utilized during the wound treatment procedure. Required medicating solution is selected by the algorithm of the microprocessor for delivery to the wound. An automated wound treatment procedure is individually tailored to conditions of the specific wound of a patient, wherein necrotic tissue and spent suspension/solution are removed from the treatment chamber by suction generated by the evacuation system to further promote wound healing.

As to still another aspect of the invention, the system further comprises an optical (e.g., fluorescence and/or reflectance) arrangement for real-time, non-invasive imaging of biochemical and/or organic substances applicable in wounds management. This arrangement provides high-resolution and/or high-contrast images. The system can be easily integrated into current wound care practice. This imaging apparatus rapidly and conveniently provides the clinician/ health care worker with biological information of a wound: including imaging of connective tissue changes, early detection of bacterial contamination/infection. The apparatus may also facilitate image-guided collection of bacterial biopsy samples.

Multiple sensors are installed within the treatment chamber to monitor different skin parameters including but not limited to temperature, melanin, hemoglobin, oxygen and water concentration in the skin, blood pressure and other heart related characteristic may be measured as well for better patient control. Using data collected by the monitoring sensors a power and control unit of the apparatus directs and controls operation of the apparatus in accordance with the treatment protocols.

BRIEF DESCRIPTION OF THE DRAWINGS

FIG. 7 is a schematic diagram of another embodiment of the apparatus and system of the invention;

DETAILED DESCRIPTION OF THE INVENTION

Figure 1:
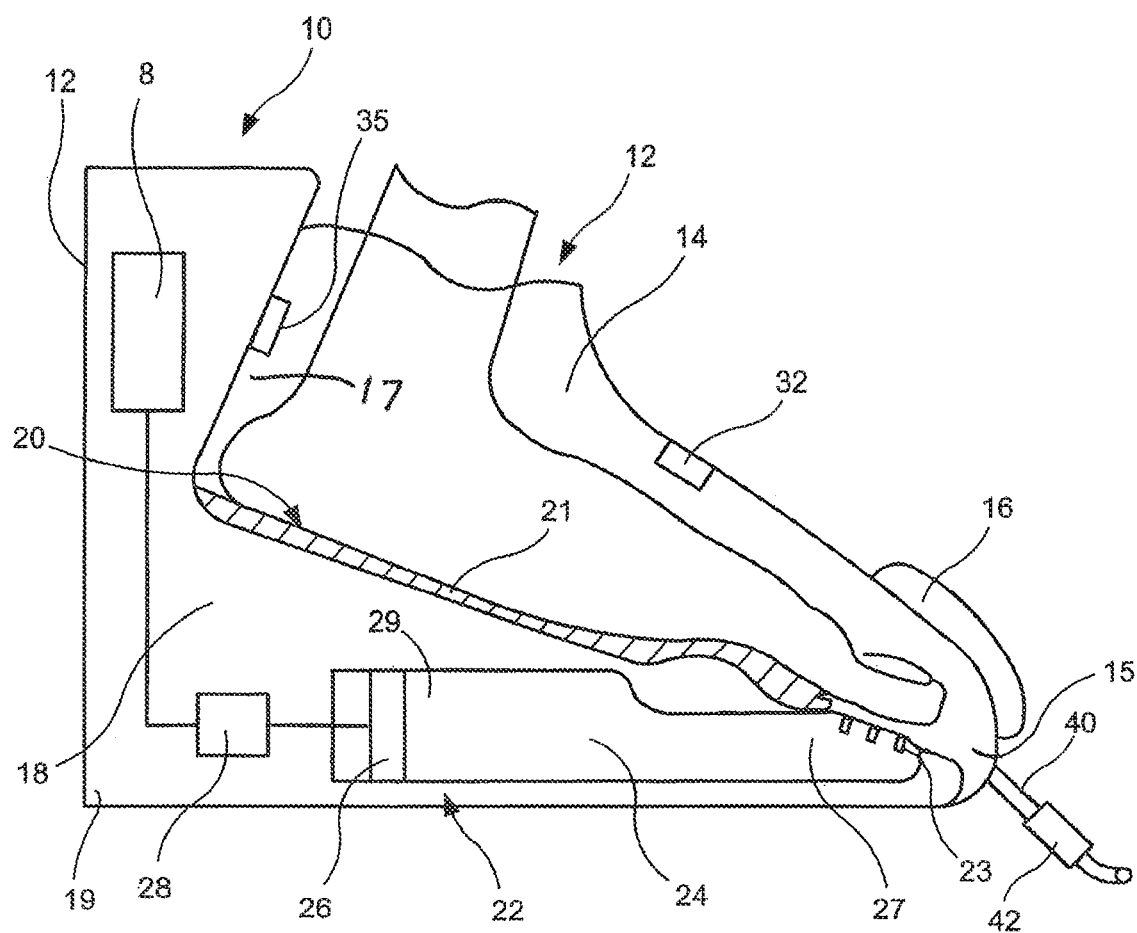
FIG. 1 is a schematic diagram illustrating one embodiment of an apparatus for treatment of foot and nail disease according to the invention.

The following terms are intended to have the following general meanings as they are used in the application.

Aqueous solution: any type of aqueous solution containing substances capable of eliminating skin pathogens including but not limited to fungus organisms, east and bacterial infection, including athlete's foot etc., treat psoriasis, acceleration of wound healing or treating any other skin disorders. Such substances are capable of either completely eliminating/destroying skin pathogens or substantially delaying reducing the rate of its growth. The treatment solutions include but not limited to the salt solution like sea water and etc., solutions containing Ethanol Alcohol, Isopropyl alcohol, p-Chloro-o-benzylphenol, o-Phenylphenol, Potassium hydroxide, dimethylbenzylammonium chloride, Lactic acid, Hydrogen Peroxide, fluconazole, itraconazole, terbinafine amorolfine, methylphenols, creosols, and any other solutions that inhibits pathogens. Treatment solution may also include substances that promote healthy skin, wound healing and/or psoriasis treatment.

Light at any wavelengths can be absorbed by a skin or nails of the patient. Such wavelengths include wavelengths selected from the continuous electromagnetic spectrum such as ultraviolet ("UV"), visible, the infrared (near, mid and far) i.e. from approximately 300 nm to 12,000 nm, etc. The light may be produced by any suitable art-disclosed Eight emitting devices such as lasers, light emitting diodes ("LEDs"), incandescent sources, fluorescent sources, flash lamps or the like. The light can be pulsed or having a continuous mode. Under Light in this invention one can understand any energy radiation that can penetrate and affect the skin tissue including electromagnetic fields, radio frequency, and acoustic including ultra sound.

The light applied during the irradiating step of the method of the invention can be supplied by a single light emitting device or a plurality of light emitting devices. Any suitable art-disclosed light emitting device(s) such as lasers, light emitting diodes ("LEDs"), flash lamps, incandescent sources, fluorescent sources, germicidal light or the like may be used to provide the required wavelength(s). Lasers include any art-disclosed lasers such as solid-state lasers, diode lasers, pulsed lasers, gas lasers, gas or vapor lasers, dye lasers, fibers lasers or diode pumped solid state lasers or the like. LEDs include any art-disclosed LEDs such as semiconductor LEDs, organic LEDS or a combination thereof. Fluorescent sources include any art-disclosed fluorescent sources such as fluorescent tubes, LED pumped fluorescent devices, cold cathode fluorescent panels or the like.

The light applied during the irradiating step of the method of the invention provides the required wavelength(s). Such wavelength(s) include wavelengths selected from the continuous electromagnetic spectrum such as ultraviolet ("UV") visible, the infrared (near, mid and far), etc. The wavelength, pulse duration continuous mode, energy density to the skin or number and repetition rate of energy pulses is optimized to achieve optimal and selective absorption in the skin pathogens or skin components like melanin, oxyhemoglobin or water as well as optimum depth of skin penetration for the best clinical efficacy outcome.

The time required for the step of exposing the infected area to an aqueous solution and the irradiating step of the method may vary depending on the existing conditions (e.g., type of the disease, the skin pathogens, the light source, the aqueous solution, the skin type, melanin concentration in the skin, hemoglobin concentration in the skin, moisture of the skin, temperature of the skin etc.). As to the irradiating step, a suitable duration will generally be from about 1 nanosecond to about 60 minutes. It is also possible and within the scope of the present invention for the light applied during the irradiating step of the therapy to be applied by a lower energy power for much longer durations (e.g., more than about 30 minutes to hours).

Referring now to the drawings, and more particularly to FIG. 1 illustrating therapeutic apparatus 10 of one embodiment of the invention which is adapted to treat toenail fungus and other medical conditions. In this embodiment the apparatus 10 is in the form of a shoe-type appliance 12 having a substantially hollow interior adapted to accommodate a treatment chamber 14. The chamber 14 extends between front 15 and rear 17 area is designed as a bath adapted to allow either one or both feet of a patient to fit comfortably and be immersed in the solution. The treatment chamber or the bath 14 is capable of holding amount of an aqueous solution required for a complete treatment of a patient. At least one energy or light source 16 is provided to allow irradiation of the foot over and around the toes and the nails. The energy source 16 is typically disposed in the vicinity of the front area 15 of the treatment chamber 14.

It should be obvious to a person skilled in the present art that the therapeutic apparatus of the invention can be also adapted for treatment of other parts of a body, which can be easily immersed into the solution contained within the chamber 14, for example, hands.

An inclined supporting platform 18 is disposed within the lower part of the interior of the apparatus. As illustrated in FIG. 1, a top surface 20 of the supporting platform is disposed at an acute angle to the bottom 19 of the apparatus. Other angles of inclination of the supporting platform to the bottom of the apparatus are within the scope of the invention. A foot of a patient is positioned within the treatment chamber 14, and supported by the platform 18 in such a manner that toenails of toes are disposed at a low level at the front area 15 of the chamber, whereas a heel of the foot is elevated at the rear area 17. In the illustrated embodiment of the invention a delivery and control system 22 for the aqueous solution is provided within the platform 18 at the vicinity of the bottom 19 of the apparatus. It should be noted however, that any alternate location of the system 22 inside or outside of the apparatus is within the scope of the invention. In the illustrated embodiment, the control system 22 consists of at least one cylinder 24 with a piston 26 slidably movable between proximal 27 and distal 29 ends thereof, and a control means or arrangement 28. The proximal end 27 of the cylinder is in fluid communication with the front area 15 of the treatment chamber 14. Control valve 23 is provided at the front area 15, so as to direct movement of the solution from the cylinder 24 into the treatment chamber 14. The control valve 23 is adapted to close communication with the treatment chamber 14 and the hollow interior of the apparatus when aqueous solution is reseeded. After being used during the treatment, the aqueous solution is discharged from the treatment chamber 14 through the discharged unit 40 which can be in the form of a pipeline initiated at the front area 15 of the treatment chamber. A filter 42 is provided at the discharge unit 40 to filter the discharged aqueous solution before it is being be re-circulated to the cylinder 24 or sent to an accumulator (not shown) for further use and/or storage.

Figure 2:
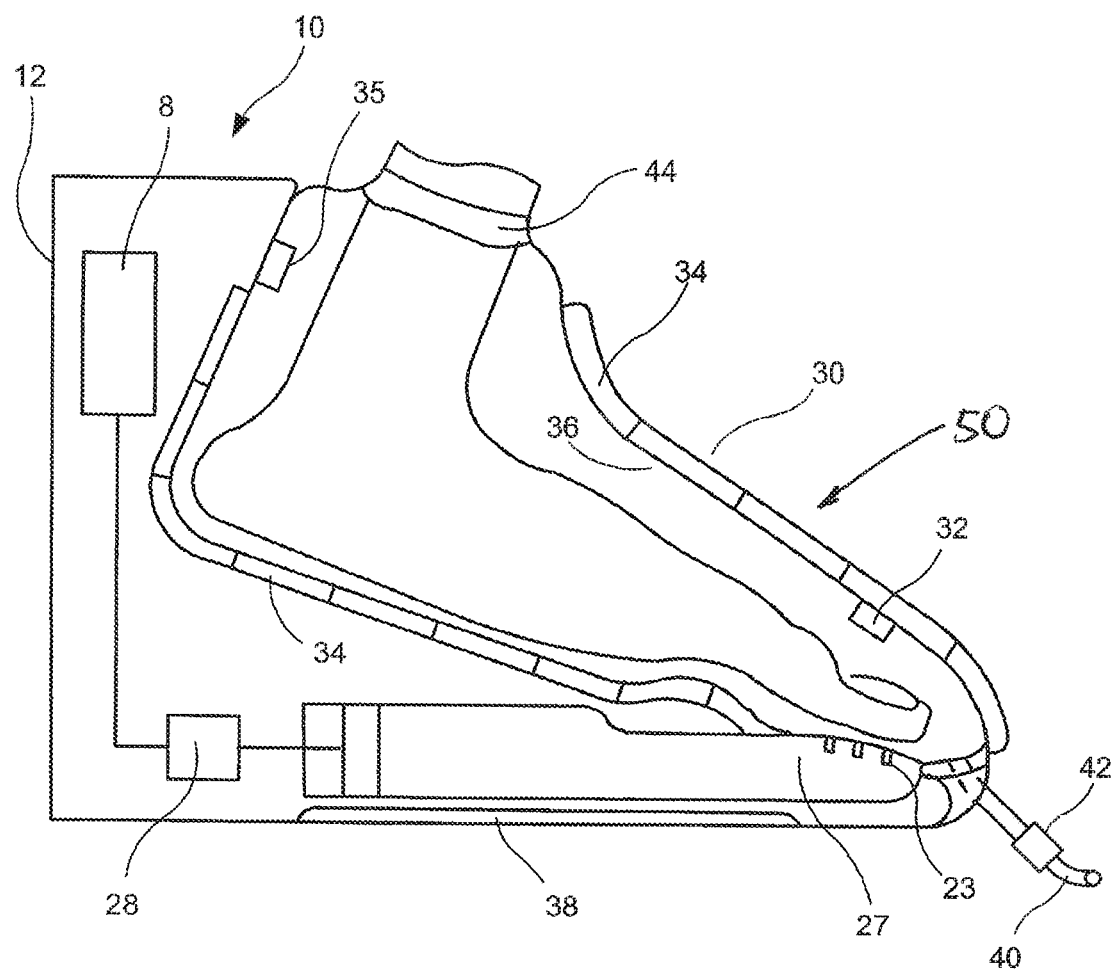
FIG. 2 is a schematic diagram of another embodiment of the apparatus of the invention.

As the piston 26 is activated, the aqueous solution through the front end 27 of the cylinder and the uni-directional valve arrangement 23 is delivered into the treatment chamber 14. During the treatment, a front of the foot with the toes and toenails, disposed at a low elevation of the front area 15, are submerged into the aqueous solution. The fungus infected toenails are washed, bathed within the aqueous solution, so that the aqueous solution flows around the infected areas. In this manner, the infected toenails are exposed to a greater degree to the medicated aqueous solution than the rest of the foot. Upon completion of this phase of the treatment, the aqueous solution is discharged from the treatment chamber 14 through the discharge unit 40 and the filter 42. As shown in FIG. 2, a resilient cuff 44 can be provided at a top portion of the treatment chamber 14 to surround an upper portion of an ankle and to prevent spillage of the aqueous solution.

In one embodiment of the invention, the top surface 20 of the platform supporting the foot is made from a resilient material. To enhance performance of the device, this resilient material is capable of adapting to a specific shape of the foot of each individual patient. As illustrated in FIG. 1, a layer of gel 21 can be disposed below the resilient upper surface of the platform. In this manner, the top surface 20 of the supporting platform closely follows the shape of the foot facilitating substantial engagement therebetween. This feature is also important in the step of irradiation, which will be discussed with reference to the embodiment of FIG. 2, where energy sources or light elements are provided near the top surface of the platform.

Figure 3:
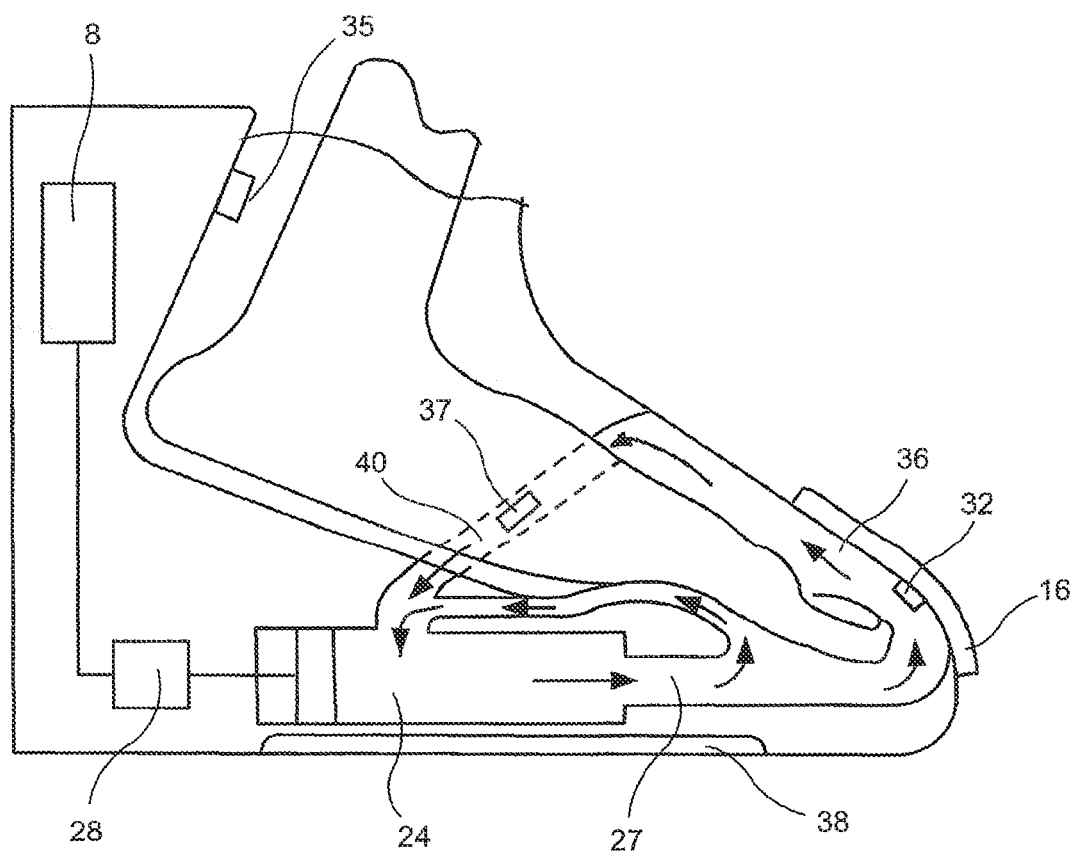
FIG. 3 is a schematic diagram of a further embodiment of the apparatus of the invention.
Figure 4:
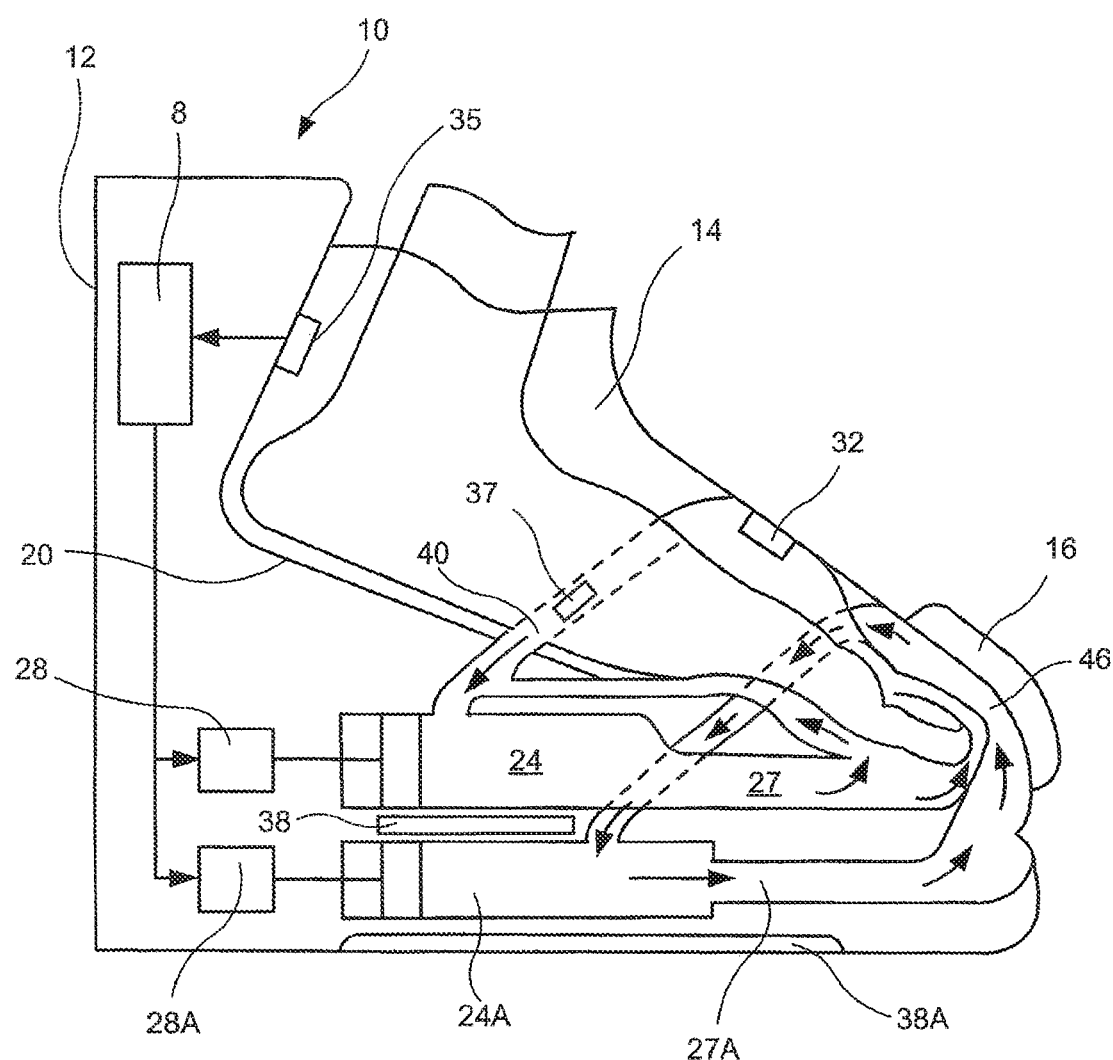
FIG. 4 is a schematic diagram of a still another embodiment of the apparatus of the invention.

As illustrated in FIGS. 2-4, a cooling arrangement in the form of at least one cooling plate 38, for example, is situated in the vicinity of the control system 22. One of the main functions of the cooling arrangement is to reduce the temperature in the treatment chamber including a temperature of the aqueous solution. Use of the cooling arrangement is especially beneficial in the embodiments where the aqueous solution is circulated within the apparatus between the treatment chamber having elevated temperature and the cylinder 24 (see FIGS. 3 and 4). As illustrated in FIGS. 3 and 4, in such systems, the cylinder or reservoir 24, the cooling plate 38 and the treatment chamber 14 are arranged as parts of the aqueous solution circulation loop 36. This arrangement allows the aqueous solution to circulate between the cylinder/reservoir 24, cooled by the cooling plate 38, to the interior of the treatment chamber 14, wherein a foot of a patient is positioned for treatment. As shown in FIG. 3, upon activation of the piston 26, the aqueous solution is being discharged from the cylinder 24 at the proximal end thereof 27 into the treatment chamber 14. After flowing around the infected areas of the foot, the aqueous solution through the circulation loop 36 is being recycled back to the cylinder 24. To facilitate efficient circulation of the solution, a circulation pump or any other similar conventional means 37 can be provided within the circulation loop 36.

Although, the cooling arrangement is in the form of the cooling plate 38 has been discussed hereinabove, it should be understood that any type of cooling arrangement provided to reduce a temperature of the aqueous solution within the treatment chamber is within the scope of the invention. For example, in an alternate embodiment of the invention, the entire supporting platform 18 is made from a resilient material, whereas an inner part of the platform is substantially hollow and filled with a cooling substance/liquid. The cooling substance cools the foot in general and the toes and toenails thereof in particular with the infected areas are treated by the apparatus and method of the invention.

In the embodiment of the apparatus shown in FIG. 4, a resilient light transparent pocket 46 filled with a cooling substance or cooling gel is provided at the front area of the chamber 14. In use the pocket 46 can adapt to the shape of the toes and toenails for a better cooling and better transmission of the light energy. The system of this embodiment is formed with at least two sets of cylinders or reservoirs 24 and 24A. The purpose of the cylinder 24 is similar to the analogous cylinders of the above-discussed embodiments, so as to provide delivery and/or circulation of the aqueous solution within the treatment chamber 14. The main objective of the reservoir 24A is to provide delivery and circulation of the cooling fluid within the auxiliary circulation loop 46. After being discharge from the reservoir 24A, the cooling fluid circulates within the light transparent pocket 46 and cools the nails area, so as to make application of irradiation energy to the nails area safer and more comfortable. The embodiment of FIG. 4 is formed with two cooling arrangements 38 and 38A. The cooling arrangement or cooling plate 38 is located in the vicinity of the cylinder 24 and provided to reduce the temperature of the solution delivered the treatment chamber 14. On the other hand the purpose of the cooling plate 38A positioned near the cylinder 24A is to reduce the temperature of the cooling solution circulating within an auxiliary circulation loop 46 adapted to cool the toe nail treatment area.

Figure 5:
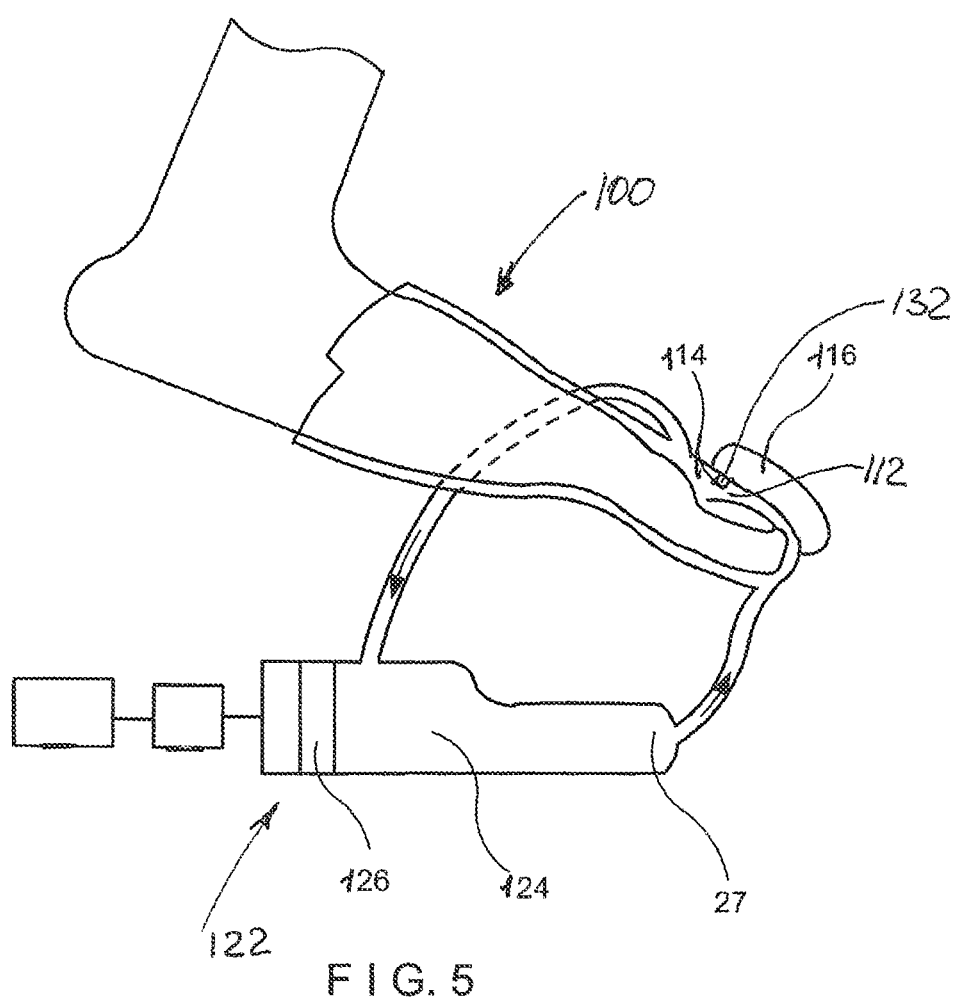
FIG. 5 is a schematic diagram of a further embodiment of the apparatus of the invention.

FIG. 5 illustrates a further embodiment of the apparatus 100 of the invention. In this embodiment, the body of the apparatus extends from the toes to about the middle of the foot with a limited treatment chamber 114 adapted to accommodate the foot front area including toes and toenails. The treatment chamber 114 includes a toe region 112 that surrounds the toes of a foot of a patient inserted thereinside. In some embodiments, toe region tapers from the inner area of the chamber to the outer area of the chamber such that it generally follows the contour of a human foot where larger toes exist at the inside of the foot, and the foot tapers to smaller toes on the outside. This can be functionally advantageous as the treatment chamber more closely conforms to the shape of the human foot. However, of ordinary skill in the art should appreciate that various shapes for toe region are within the scope of the invention.

Although, the apparatus 100 is formed with the treatment chamber 114 adapted to accommodate various sizes of human foot, an apparatus with a custom-formed treatment chamber designed to accommodate a custom foot configurations of a specific patient is within the scope of the invention. Such custom configured chambers are especially useful for patients with substantial foot deformities, as well as invalids having a part of a foot being removed, etc.

The apparatus of the embodiment illustrated in FIG. 5 is typically made from a resilient material such as rubber, for example. At least one energy light source 116 is provided at the proximal end of the chamber for irradiation of the foot in general and the toes and nails specifically. A tightening arrangement, such as a cuff 44 for example (see FIG. 2), can be formed at the distal end of the chamber to facilitate tight connection between the apparatus and the foot of the patient and to prevent leakage of the aqueous solution from the treatment chamber.

In the embodiment of FIG. 5, the delivery and control system 122 for the aqueous solution is situated outside of the apparatus. Similar to the above-discussed embodiments, the liquid control system 122 may include a cylinder 124 with a piston 126 movable thereinside. During the treatment, the front of the foot, including the toenails is submerged within the aqueous solution provided within the treatment chamber. A sensor 132 can be provided within the treatment chamber to further control the treatment process.

The resilient material used for manufacturing of the apparatus 100 is impermeable to the aqueous solution. In view of the relatively low cost of production, the apparatus is disposable in nature. The apparatus is convenient for specific treatment sessions arranged for particular patients. The control system 122 positioned outside of the apparatus is reusable and can disconnected from the treatment chamber 114 upon completion of the prescribed treatment. If needed, the control system 122 can be re-connected to another unit. Such arrangement provides substantial cost saving to an operator.

Figure 6A:
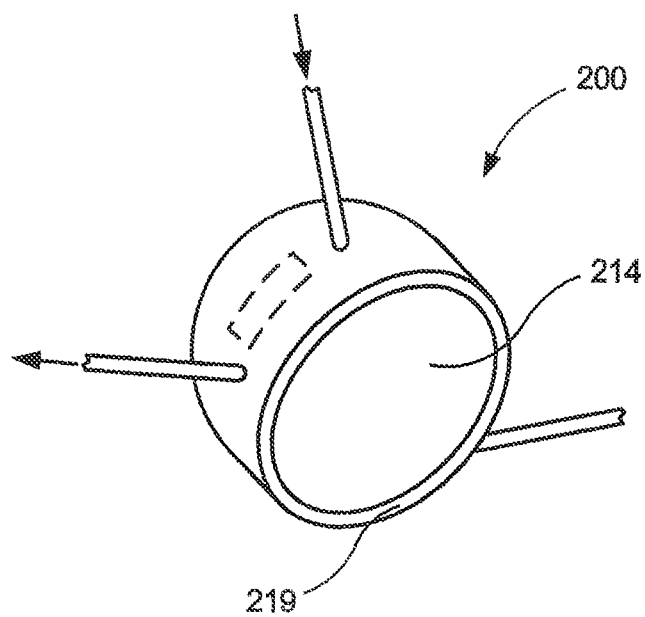
FIGS. 6A and 6B are schematic diagrams of an alternate embodiment of the apparatus of the invention.
Figure 6B:
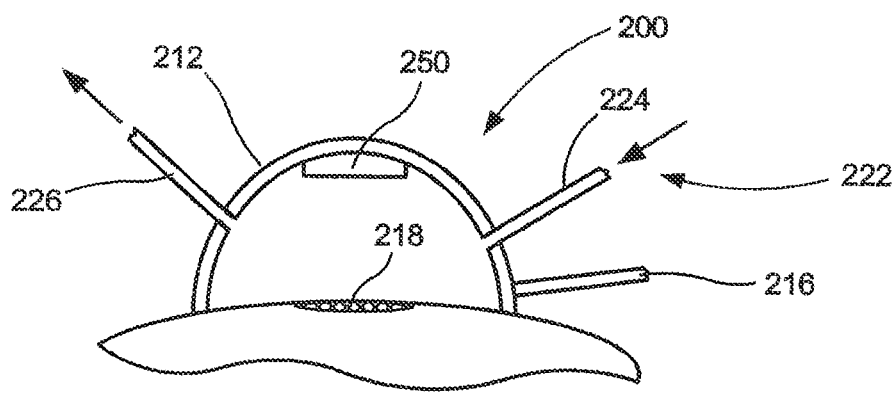

As indicated above, multiple embodiments of the apparatus of the invention including various treatment chambers can be used and adapted for different clinical applications. FIGS. 6A and 6B show the embodiment of the apparatus 200 of the invention provided for treatment of wounds and skin conditions 218 practically at any part of human body. The body 212 of the apparatus has a semi-spherical configuration with a hollow treatment chamber 214 formed thereinside. A vacuum arrangement 216 is provided to create a vacuum within a hollow space 219 formed between the walls of the treatment chamber 214, which are in contact with the skin. This arrangement facilitates better engagement between outer periphery of the body and the skin area to be treated. A delivery and control system 222 for the aqueous solution consisting of inlet 224 and outlet ports 226 is provided. A radiation energy source 250 is disposed within the chamber 214.

The light delivery arrangement 50 of the present invention includes a light source, an energy source in power communication to the light source; and a controller that controls amount and/or duration of light to be applied to the patient by the light source and sensors 32, 35 to measure skin/nails characteristics.

As discussed above, the light source can be any suitable art-disclosed light emitting device(s) such as lasers, LEDs, incandescent sources, fluorescent sources, or the like may be used to provide the required wavelength(s). A light source can be a visible infrared light generated by any conventional sources, including light bulbs, impulseable laser as well as the devices capable of absorbing and concentrating the sunlight.

In the embodiment of the invention illustrated in FIG. 2, the light source 34 is an array of LEDs or other energy sources. In another exemplary embodiment, the light source is an array of optical fibers powered by a laser. The apparatus of the invention also includes an energy source in power communication with the light source and is adapted to provide power to the light source. The energy source can be DC and/or AC. The housing of the apparatus can optionally be adapted to contain an autonomous energy source (e.g., batteries or the like). Alternatively, the energy source can be located outside of the housing but is in power communication with the light source via any conventional means, including cable(s). The apparatus further includes a controller that controls the amount (including duration) of the light that is applied to the treated area.

One embodiment of the device and method of the invention involve use of arrays of light emitting diodes (LEDs), comprising at least one set of LEDs which emit light at the required wavelength. The set of LEDs is configured within the array in predetermined patterns and is activated at the required frequency in sequence for predetermined durations of time. In certain aspects of the invention, treatments are provided involving inserting the limb into the device, adjusting for comfort, and activating the device for a pre-programmed treatment of approximately 5-45 minutes.

When a laser is utilized as a light source, the generated beam is controllably absorbed in the target tissue at the required depths.

Utilization of a laser in the present invention as a light source is accompanied by automatic target thermal feedback to precisely control the dosimetry of the laser, intense light or intense pulsed light irradiation. This is needed to prevent damage to surrounding tissue and reduces pain. For this purpose, a non-contact thermal detector can be provided. The output of the non-contact thermal detector is used to adjust the power output of the laser to maintain a selected treatment temperature at the treatment site.

In the invention, absorption of laser energy by the nail bed of the infected toe or finger results in a controlled elevation in temperature, to a temperature effective of disinfection at the infected regions or areas. In the invention, this occurs without causing irreversible thermal damage to the infected nails. The laser control system of the invention adjusts the energy to maintain a pre-selected target temperature at the spot. In one embodiment of the invention, to maximize patient comfort and safety, an optional continuous or pulsed cooling device can be provided to deliver a stream of coolant to the target treatment spot during or after each laser treatment session.

As best illustrated in FIGS. 1, 2, 3 and 4, energy or light source(s) 16 is disposed within front part of the apparatus in the vicinity of the treatment chamber 14, which is adapted to accommodate toes and toenails of a patient and additional energy or light sources to provide energy irradiation to all other skin areas.

To further control the treatment process, a sensor 32 is provided within the treatment chamber 14. The sensor 32 is capable of detecting the level of melanin, hemoglobin or water/moisture content, etc., within the skin of a patient positioned within the chamber. Thus, optimal levels of radiation can be achieved for each zone of treatment. For example, a higher level of radiation can be provided at the front area 15 of the treatment chamber 14 which accommodates toes and toenails infected with a fungus. On the other hand, lower levels of radiation will be generated and directed to the areas of the treatment chamber accommodating a heel and the surrounding regions of the foot. To further control the treatment a condition of the surrounding tissue is monitored by a detecting arrangement or detector 35 adopted to detect irradiation reflected from such tissue. One of the main functions of the detector 35 is to control the effect of the energy or light source on the surrounding tissue of a patient. In every individual case a doctor sets specific characteristics of the irradiation to produce the required effect. If situation in the treatment chamber become unfavorable, for example the temperature exceeds predetermined limits, the detector 35 generates a signal directed to the control unit 8 which in turn produces a correcting signal to the power unit or to the control arrangement 28 of the cooling system 22. This in turn energizes circulation pumps 37 and/or cooling plates 38, so as to directly and indirectly lower temperature in the treatment chamber 14. Similar signals can be also produced when the prearranged levels of the energy density, power density or other characteristics of the operating laser are attained. This is necessary to exclude possibility of damaging an adjacent healthy skin tissue. The detecting arrangement 35 can be made utilizing a wide variety of photoelements, photoresistors, photodiodes and similar devices.

In the embodiment of the invention illustrated in FIG. 2 a plurality of energy sources 34, such as an array of LEDs for example, are disposed within the walls of the treatment chamber formed within the hollow interior of the apparatus. Although the multiple energy sources can be randomly provided, in the illustrated embodiment such energy sources 34 are uniformly distributed through the inner surface of the treatment chamber.

In a further embodiment of the invention, the inner surface of the treatment chamber 14 is covered by a light reflective material. In this manner, the energy of the light sources disposed at the reflected layer are fully reflected and directed to the foot positioned within the treatment chamber 14.

The method of the present invention also includes the steps of irradiating the infected area with the light or energy sources 16, 34 at a wavelength absorbed by skin chloroforms including but not limited to melanin, hemoglobin, oxyhemoglobin, or water in the skin or nails of a patient, so as to destroy fungal and/or bacterial infection, and/or microbes, and/or coagulate contaminated or diseased tissue in the nail, under the nail, in the nail matrix or at any other affected are of the skin. Since light can penetrate through the skin and through the nail, the irradiating step is achieved by irradiating either directly or indirectly through the nail with a light source at the required wavelength, so as to destroy infected material on the nail bed as well as in the matrix below and around the nail bed.

In the method of the invention, the steps of treating the infected area by an aqueous solution and the step of irradiating the infective area with a light source can be conducted separately/independently of each other or in combination.

We are referring now to FIG. 7 illustrating another embodiment of the apparatus and system for treatment of wounds and skin medical conditions at a predetermined skin area of human or animal. Among essential elements of the system are a treatment assembly 300 consisting of a treatment device with a housing 310 formed with a fluid delivery mechanism 322 and an evacuation suction system 340. The treatment assembly includes a handheld device 360 containing a laser source or emitter 362, an image recording device 366, a scanner 364, multiple sensors 368 and a control unit 370

As illustrated in FIG. 7 the treatment device/apparatus having a housing 310 is formed with a hollow treatment chamber 312 defined in the interior of a semi-cylindrical peripheral wall 314 extending between a closed top region 316 and an open bottom region 318 to be disposed at a wound treatment area 320. The top region 316 is made of a material translucent to the laser and other types of radiation. Although the treatment housing having specific shape of the peripheral wall has been described, it should be noted that any conventional configuration of the peripheral wall provided to accommodate various sizes and shapes of wounds is within the scope of the invention.

In the wound treatment method of the invention a user is provided with an advantageous step of selecting a (disposable) treatment device or vessel 310 which accommodates multiple wound characteristics, including size, shape, intensity, healing stage etc. of a specific wound at a predetermined skin area. Thus, each patient is provided with his own/personalized treatment vessel accommodating specific wound characteristics. Different sizes of the vessels are used for different sizes of wound. A variety of disposable kits is provided for treatment of certain types of wounds containing medications and other liquid, gaseous including pressurized oxygen or other substances that may be used in the wound treatment procedure using the FIG. 7 wound treatment device functionalities. Each kit contains predetermined drugs in quantity and concentration stored in containers 328. For example, to treat the wound there will be an option of using, for example, five drugs. Respectively there will be a package/container 328 divided into five parts or five cartridges connected to a dispensing nozzle 326. To improve visualization of the treatment process carried out in the treatment chamber the peripheral wall 314 can be made of a transparent or translucent resilient elastomeric material.

The treatment device 310 selected to optimally match the size and body location of the wound of a specific patient is attached to the handheld device 360 containing multiple components of the system. The device selected in the above-discussed manner allows for tight contact with the skin surrounding the wound area. Such device allows optimal access to the wound through its internal cavity area for the laser light energy, photo/video camera, detectors, delivery of medication and treatment solutions as well removal of debris and by products of wound debridement and treatment. Further advantages of the treatment housing 310 invention involve multiple ports integrated into the peripheral wall 314 that allow creation of a negative pressure zone in the treatment chamber 312 near the wound treatment area 320. Some of the ports supply and remove multiple types of aqueous and gaseous solutions which may contain medications or other chemicals useful in the treatment or debridement of the wound.

A medication delivery mechanism 322 including nozzle 324, a pump 326 are provided for supplying meditative debridement liquids/fluids to the wound treatment area 320 from the containers 328. Multiple storages/containers 328 store and control different types of wound treatment substances and materials applied to the wound treatment area 320 through and using the disposable vessel. The wound treating solutions may be oxygenized before being supplied into the treatment chamber. Cooling arrangements 329 are preferably provided between the containers 328 and the pump 326 for cooling the debridement liquids/fluids or chemicals prior to delivery to the treatment chamber. In the illustrated embodiment the nozzles 324 are situated at the bottom region 318 of the treatment chamber. To assure even application of the liquids throughout the treatment area 320, in one embodiment the multiple nozzles 324 are formed at the circumference and different elevations in the peripheral wall 314. By means of the pump 326 the debridement fluids/chemicals are supplied/dispensed from exterior containers 328 through the nozzles 324 to the wound treatment area 320 situated within the treatment chamber.

The nozzles 324 swirl the debridement fluids/chemicals or gaseous substances in the treatment chamber in the skin vicinity to wash or treat the wound. The streams of debridement fluids exiting the nozzles 324 are regulated by the pump 326, controlled by the algorithm of the microprocessor 372 of the control unit 370. As discussed in greater detail below, the application of the debridement liquids to the treatment area 320 is controlled/determined by the algorithm of the microprocessor 372 of the control unit 370 based on the analysis of various factors including the pictorial data/photograph/films produced by the cameras 366 and sensors 368, 374 situated in the treatment chamber.

The diagram of FIG. 7 schematically depicts a system 340 for evacuation of the debris from the debridement and spent liquids from the treatment chamber 312 during the debridement process and to ultimately promote wound healing. At least one suction outlet or debris removal socket 342 is provided at the bottom region 318. By means of a connector 344 passing though the peripheral wall 314 the suction outlet is connected to other components of the evacuation system 340 situated outside the treatment vessel 310. An exterior vacuum pump 346 is connected to the suction outlet 342 by to create a low-pressure zone resulted in suction pressure within the bottom region 318 of the treatment chamber 312 to evacuate the debris and spent liquids directly from the operating site. Suction outlet may optionally include a grid of blades to cut the debris of debridement to facilitate the aspirating of debris.

In an optional embodiment, the vacuum pump 346 is interconnected to a pulse modulator 348 to form one or more pressure differentials to the evacuation system. Accordingly, by the use of the pulse modulator 348, rather than creating a constant suction pressure within the evacuation system 340, to remove the debris and or debrided necrotic tissue from the wound treatment area 320, the alternative pressure is applied, thereby creating pulses of suction pressure within the treatment chamber 312. Utilizing a series of constant and/or varying pressure pulses is potentially beneficial in aspirating necrotic tissue, particularly when aspirating larger tissue pieces is needed.

An aspirated necrotic tissue from the treatment chamber 312 is accumulated and stored in the disposable debris storage container 350. A filter or sampler 352 can be also provided upstream of system for aspirated tissue material collection for further analyzing the type, quantity, and flow rate of the tissue material being removed from the wound treatment site. The debris container 350 may be in fluid communications with the vacuum pump 346 and may include one or more known devices for collecting and filtering tissue materials removed from a patient. The container 350 may have transparent sidewalls for providing visual feedback to a user regarding content, coloration, etc. Those of skill in the art will appreciate that various types of collection containers may be used. The collection container 350 and/or filter 352 may also comprise one or more custom filter features with various mesh sizes, capacities, etc. based on the specific application.

As an optional feature, miniature heat sinks or small mechanical fans, or other heat dissipating devices may be provided in the treatment chamber 312 to allow excess heat to be removed. The treatment device 310 may be powered using standard AC/DC power and/or by rechargeable battery pack.

The device 300 may also be associated with or mounted to an external mechanical apparatus (e.g., tripod, or movable stand with pivoting arm) allowing mobility of the device within a clinical room with hands-free operation of the device.

Operation of the system of the invention is carried out and controlled by a control unit 370 having a microprocessor 372. Among various functions of the system the control unit regulates operation of the laser source 362 for the optimum output level based on type and characteristics of the targeted wound treatment area. It will be discussed later in the application in greater detail that characteristics of the control unit 362 may be adjusted by the operator or automatically based on inputs from the sensors 368, thermal detector 374 and video images generated by the imaging apparatus 366.

As illustrated in FIG. 7, the treatment assembly is formed with a laser handheld device 360 securely and releasably connected in any conventional manner to the top region 316 of the treatment housing. Among essential components of the system/device of the invention provided in the handheld device 360 are: a laser source or emitter 362; a scanning device 364, an image recording device 366 and multiple sensors/detectors 368 situated at a connecting area 365 forming an interface between the handpiece and the top region 316.

An essential function of the scanning device 364 is to target and position the laser beam 367 at the proper part of the wound for the optimal period of time to thoroughly cover the wound area 320 in an optimal laser pattern.

The sensors or detectors 368 detect and measure concentration of various substances in the wound including but not limited hemoglobin, melanin, water, different bacteria and materials produced by such bacteria, etc. Another function of the sensors 368 is recognize (determine) the physical and chemical properties of the wound (moisture content, for example). The sensors 368 emit and receive various types of signals (optical, electromagnetic, acoustical, capacitance measuring). The microprocessor 372 forming a part of the control unit 370 receives and analyzes data obtained by the sensors 368 and generates signals to adjust parameters of the laser 362, the liquid dispensing nozzles 326 and the suction outlet 342 to optimize the debridement of necrotic tissue and/or treatment of the wound or to produce other desired effect on targeted wound area 320, so as to ultimately to promote wound healing.

Utilization of the device of the invention may be also accompanied by automatic target feedback, thermal feedback for example, to precisely control the laser application. This is needed to prevent damage to surrounding tissue. For this purpose, non-contact thermal detectors 374 can be provided. The output of the non-contact, thermal detectors 374 provided in the treatment chamber 312 and used to adjust the laser output to maintain selected characteristics including temperature at the wound treatment site 320.

In an alternate embodiment the control signal generated by the thermal detector 374 energizes the medicative liquids nozzles 374 and cooling arrangement 329 which ultimately directly or indirectly lower/adjust temperature at the wound treatment site, to exclude possibility of damaging an adjacent tissue. The detector 374 and the sensors 368 can be made utilizing a wide variety of photoelements, photoresistors, photodiodes, electric capacitor sensors and similar devices.

The laser energy applied to biological tissue of the wound treatment area 320 is generated by the laser source 362 disposed in the interior of the hand piece 360. Laser energy may promote wound healing by multiple mechanism of action. Optimally configured laser energy may precisely and controllably ablate or vaporize the necrotic layer of the wound tissue. It disinfects the wound, kills bacteria and effectively sterilizes a pus. Thus, the pus is not removed, but disinfected by the laser energy. In traditional methods of wound debridement, a scalpel or blade is used to cut or scrape the necrotic tissue and/or infected pus from the wound surface. Scraping the wound surface with scalpel or blade inevitably result in scraping of the healthy layers of wound tissue including the newly grown layer of collagen cells (so as to remove the healing layer). As result with each mechanical debridement the healing process is reversed and set back which often result in creating a chronic wound condition where patient' healing power is not sufficient and can not overcome the constant disturbance of the wound by traditional mechanical debridement options. Additionally, it has been clinically proven that certain types of laser energy produce or promotes the collagen formation as well as may promote a new vasculature formation that can be helpful to increase supply of vital components for wound tissue regeneration. Collagen growth is one of the main conditions for the healing process.

In the wound treatment using the apparatus of the invention laser irradiation promoting the wound healing may include range of wavelengths between 300 nm to 12000 nm, pulse duration from $10^{-9}$ (femtoseconds) to $10^{-3}$ milliseconds, laser intensity (fluence) to the wound from millijoules per squire cm to tens of joules per square cm. Total amount of laser energy applied, number of laser pulses with certain set parameters, repetition rate of laser pulse applied, and other laser parameters are being optimally adapted based on the condition of the wound including but not limited to presence of necrotic tissue, bacteria, inflammation, melanin concentration (color of the skin), location on the body, size etc.

Nd:YAG 1064 nm or similar laser energy with pulse duration below but close to the thermal relaxation time of skin tissue of 800 microsecond is particularly beneficial because this pulse duration allows for delivery of higher energy density to the skin without creating of burns and pain to the patient compare with other pulse durations but also allows for a deep penetration of the laser energy into the treated tissue. 1064 nm laser energy with pulse duration below 800 microseconds is known to promote collagen regrowth, which is beneficial to wound healing process. The pulse duration in vicinity of 650 microseconds are particularly optimal for the wound healing applications.

Another optimal wavelength particularly applicable for wound debridement application is 2940 nm Er:YAG laser energy with 100-1000 microsecond pulse duration. Such energy allows for very superficial and controllable vaporization of the top surface of the wound for an optimal removal of necrotic tissue or infected materials from the surface of the wound. 2940 nm Er:YAG laser energy with 200-300 microsecond pulse duration and fluence below 10 j/cm2 is particularly optimal because it allows for vaporization of the top layer of the wound without creating thermal damage to the not vaporized wound tissue. This allows for precise and controllable removal of necrosed wound tissue and/or infection.

The microprocessor 372 of the control unit 370 is processed by certain algorithm to control the parameters of the laser device 362 energy with optimally selected parameters including wavelength, energy level, pulse duration, and others.

In the invention generated laser beam 367 is controllably absorbed in the target tissue in the wound treatment area 320 at the required depths of the wound. Utilization of a laser for the wound treatment may be accompanied by automatic target thermal feedback to precisely control the dosimetry of the laser or other energy used for wound treatment or debridement including but not limited to intense pulsed light, radiofrequency, ultrasound, shockwave, plasma or other forms of electromagnetic energy. This is needed to prevent damage to surrounding tissue and to reduce pain. For this purpose, a non-contact thermal detector 374 can be provided. The output of the non-contact thermal detector is used by the control unit 370 to adjust the power output of the laser to maintain a selected treatment temperature at the treatment site.

Absorption of a laser energy by the predetermined wound skin area 320 selected for treatment results in a controlled elevation in temperature, to a temperature effective for the wound treatment at the designated areas. In the invention, this occurs without causing irreversible thermal damage to the surrounding tissue. The control unit 370 adjusts the energy to maintain a pre-selected target temperature at the spot. The temperature elevation occurs controllably without causing irreversible thermal damage to the tissue surrounding the treatment site. The control unit 370 adjusts the energy to maintain a pre-selected target temperature at the site. To maximize patient safety, the continuous or pulsed cooling devices/units 329 are activated by the control unit 370 to deliver streams of cooled liquids from an infusion material storage containers 328 by the infusion pumps 326 and the nozzles 324 to the wound treatment site 320 during or after each laser treatment session.

The image obtaining apparatus 366 (which can be in the form of photo or video camera) is disposed in the vicinity of the laser hand piece connecting area 365 at the interface between the handheld piece 360 and the top region 316 of treatment chamber. The main function of the apparatus 366 is to obtain and record images of the wound treatment site 320 at different wavelengths to assess the different characteristics of skin medical conditions, including size, configuration and depth of the wound. The imaging apparatus 366 may be a digital camera having a touch-sensitive viewing and/or control screen, image capture and zoom controls and provided with a wired and/or wireless data transfer port/module and, an electrical power source and power/control switches. It is operable at different wavelength in the environment providing/supporting both illumination and/or reading function. The image obtaining apparatus 366 allows control unit, microprocessor and/or practitioner either by highlighting a wound at certain wavelengths, or highlighting certain wavelengths in a reflective signal, to determine the presence of some chemical or biological substances/compositions in the wound tissue and/or skin tissue surrounding or forming a part the wound.

A source of monochromatic or mixed wavelength light can be provided to illuminate a wound in an optimal wavelength light to make photograph recordings of the concentration of different substances in the wound including but not limited hemoglobin, melanin, water, necrotic tissue, different bacteria and materials produced by such bacteria.

By analyzing the recorded data of these substances, a control unit, a microprocessor and/or practitioner can determine the status and the progress of wound healing and optimally calculate the next steps sequence necessary for optimal wound healing treatment. The progress of the wound treatment is determined through evaluation of images obtained at different wavelength to confirm whether the area of the wound is being reduced or enlarged. Another important characteristic which can be ascertained from the obtained images is a color of the wound and its internal structures. The obtained images can address the state of biological components and bacteria, enabling an operator to see the infected tissues inside the wound, and determine formation of vessels and the build-up of collagen.

Another essential functionality of the imaging apparatus 366 is measuring the wound, which provides an objective characteristic of the progress of the wound healing process. Algorithm in the laser control microprocessor 372 can use the wound images to position the area to be treated with the laser and guide laser beam scanning mechanism 364 to thoroughly cover the wound area 320 in an optimal pattern for better efficacy and safety avoiding overheating.

The sensors 368 generate a signal directed to the control unit 370 which facilitates measuring hemoglobin concentration in the wound, to allow access the level of inflammation in the wound which is an important characteristic of the healing process. The temperature detector 324 provides data to the control unit 370 to optimally control the amount of laser energy applied to the wound area 320 and is used to control energy in the pulse, pattern and repetition rate of laser pulse application to the wound. Measuring melanin in the treated wound is used to tailor the energy pulse level.

All data generated/produced by the image obtaining apparatus 366, sensors 368 and thermal detector 374 is transferred to a memory of the microprocessor 372 in the control unit 370 for sorting and processing. This data is retained in the memory of the wound healing data base 376 or a hospital data base 378 as a part of the patient's medical history, enabling to record progress of the treatment. Based on the data reflecting the wound behavior an algorithm of the microprocessor 372 generates instructions for the delivery mechanism 322 as to what pharmaceutical or chemical ingredients can be used for cleaning/treating the wound to reach the required therapeutic effect. Such instructions may also contain recommended concentration of the substances and composition for gases and/or fluids utilized for cleaning the wound. By exploiting wireless capabilities with image analysis and diagnostic algorithms, the device may be integrated into telemedicine (e.g., E-health) infrastructure for remote-access to specialists in wound care.

In the invention to effectively control removal of the necrotic tissue, a condition of a tissue surrounding the operation site is monitored by the sensors 368 adapted to detect irradiation reflected from such surrounding tissue. One of the essential functions of the sensors 368 is to control the effect of the necrotic tissue removal on the tissue surrounding the site. In every individual case a doctor sets specific characteristics to produce the required effect. If a situation at the wound treatment site becomes unfavorable the sensors 368 generate a signal directed to the control unit 370, which in turn produces a correcting signal to the laser 362.

The control unit 370 also includes software allowing a user to control imaging parameters, visualization of images, storage of image data and user information, transfer of images and/or associated data, and/or relevant image analysis (e.g., diagnostic algorithms).

Through a connection to a centralized network, the control unit 370 and the microprocessor 372 allows upon processing the data, to send appropriate information to insurance companies and/or social medicine services for payment and reimbursement. In the treatment of wounds there are certain protocols for which different chemical medical substances can be used in different concentrations.

Figure 8:
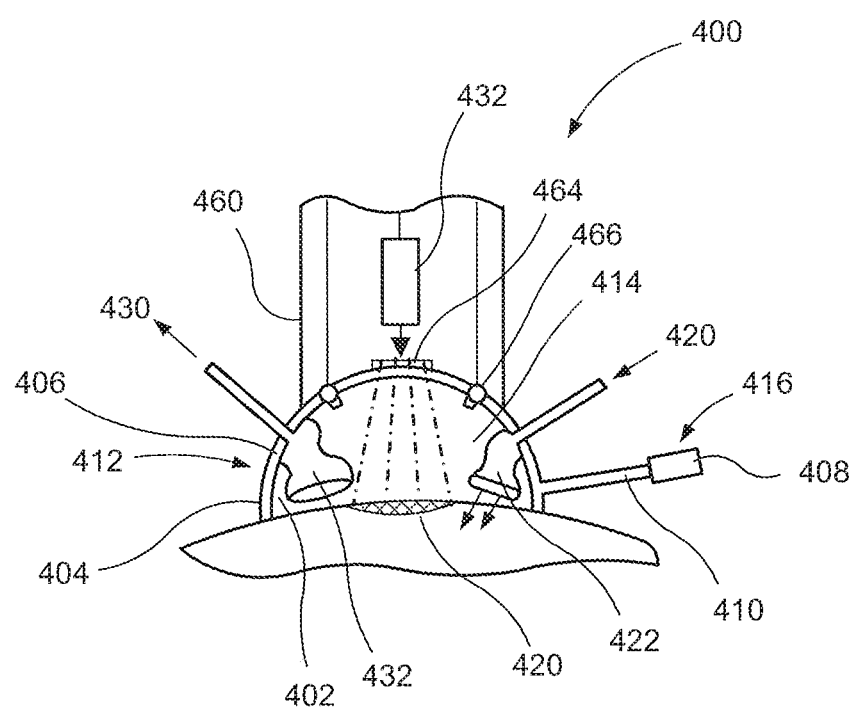
FIG. 8 shows a further embodiment of the apparatus of the invention.

Referring now to FIG. 8 illustrating another embodiment of the wound treatment device 400 of the invention. The body 412 of the apparatus is formed by spaced from each other inner 402 and outer 404 walls having semi-spherical configuration with a hollow treatment chamber 414. An isolation vacuum arrangement 416 is provided to create a vacuum within a hollow space 406 formed between the walls 402, 404. An auxiliary vacuum pump 408 provided outside of the device 400 and connected to a suction conduit 410 creates a low-pressure zone resulted in suction within the hollow space 406. This arrangement facilitates better engagement between outer periphery of the body 412 and the wounded skin area 420 to be treated. Thus, whole skin segment surrounding the treated skin area 420 is completely isolated from outside influence during the treatment cycle.

In the embodiment of FIG. 8 delivery mechanism 420 for the aqueous solution is provided with a nozzle 422 situated in the treatment chamber 414. Although not completely illustrated, operation of the mechanism 420 is similar to that of FIG. 7 embodiment and includes the pump, the containers for supplying dispensing medicative debridement liquids/fluids at the wound treatment area 420 among other elements. A system 430 for evacuation of the necrotic tissue and spent liquids from the treatment chamber 414 includes a suction outlet 432 connected to other components of the evacuation system such as a vacuum pump, debris container, etc. situated outside of the treatment cup. Although not illustrated in full detail, operation and components of the evacuation system 430 are similar to the analogous system 340 disclosed in the embodiment of FIG. 7. As illustrated in FIG. 8, the treatment assembly is formed by a hand piece 460 releasably connected to the top region of the treatment device 400. Similar to FIG. 7, essential components of the system/device of the present embodiment of the invention include: a laser source 432, a scanning device 464, an image recording device 466 and multiple sensors/detectors 468 situated at a connecting area forming an interface between the handpiece 460 and the body 412.

Figure 9A:
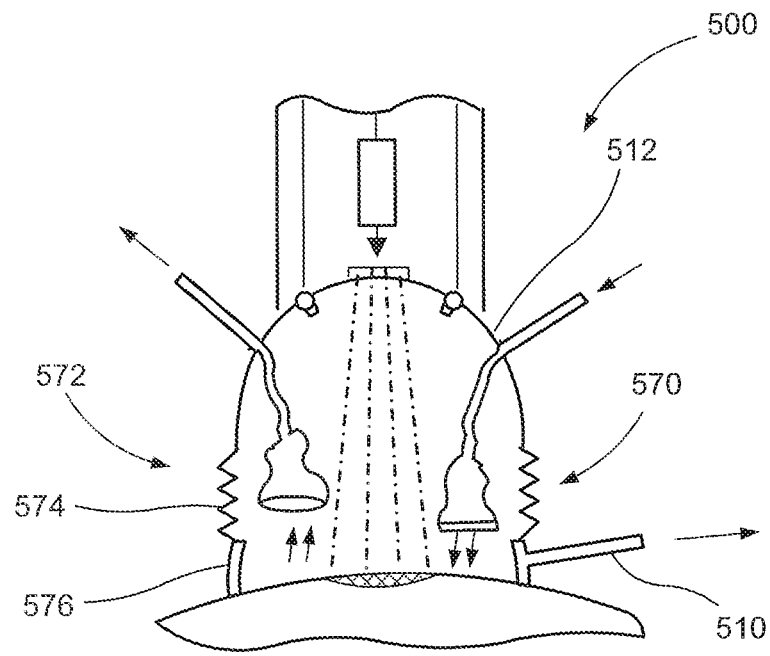
FIGS. 9A and 9B illustrate modified embodiments of the apparatus of FIG. 8.

Referring now to FIG. 9A illustrating still another embodiment of the wound treatment device 500 of the invention. This embodiment is similar in many respects to the wound treatment device of FIG. 8, with the exception of the bellow type formation 570 provided in the semi-spherical body 512 of the apparatus. The expandable bellows 570 are formed in the central part of the body peripheral wall having a series of pleated folds 572 forming an accordion folding area of the treatment chamber 514. Due to this feature the treatment chamber is allowed to expand vertically from a compressed state having a regular or limited interior space to an expanded state having substantially increased interior space.

In the embodiment of FIG. 9A the double wall construction of the body forming the isolation vacuum arrangement 576 is limited to the bottom region of the treatment chamber and does not to extend to the bellow type formation 570.

Figure 9B:
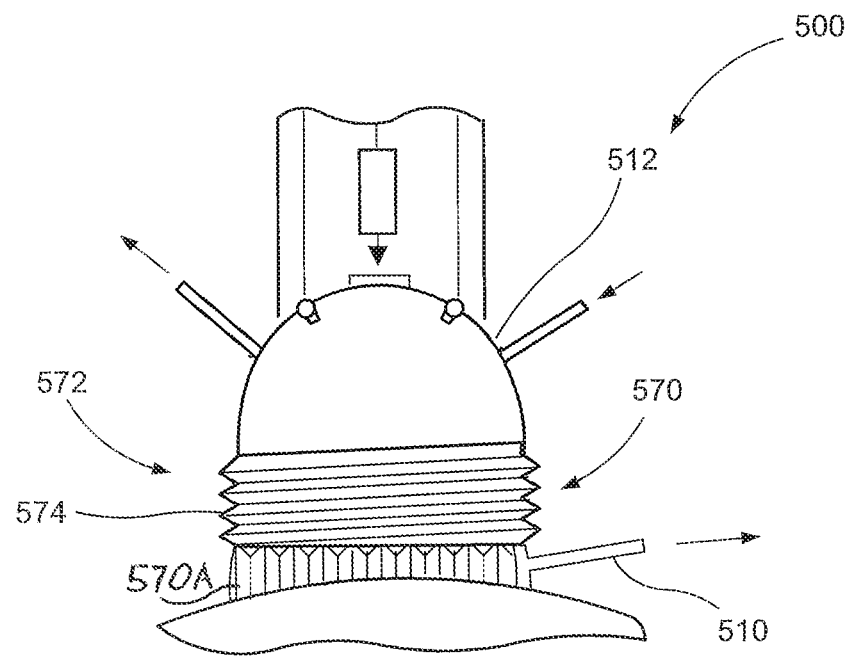

The embodiment of FIG. 9B is formed with an accordion folding walls 570A so that the treatment chamber 514 is also allowed to expand horizontally and circumvent a larger wound area with tight seal for wound treatment procedure. The bellow type formations 570, 570A further enhance versatility of the of the invention, wherein one wound treatment apparatus can accommodate wounds having different sizes and simplifies the apparatus selection step of the method of the invention.

The expandable bellows 570, 570A can be made from a resilient material, and specifically can be made of an elastomeric material that retains a natural resiliency that tends to expand to its expanded fully deployed length.

Figure 10:
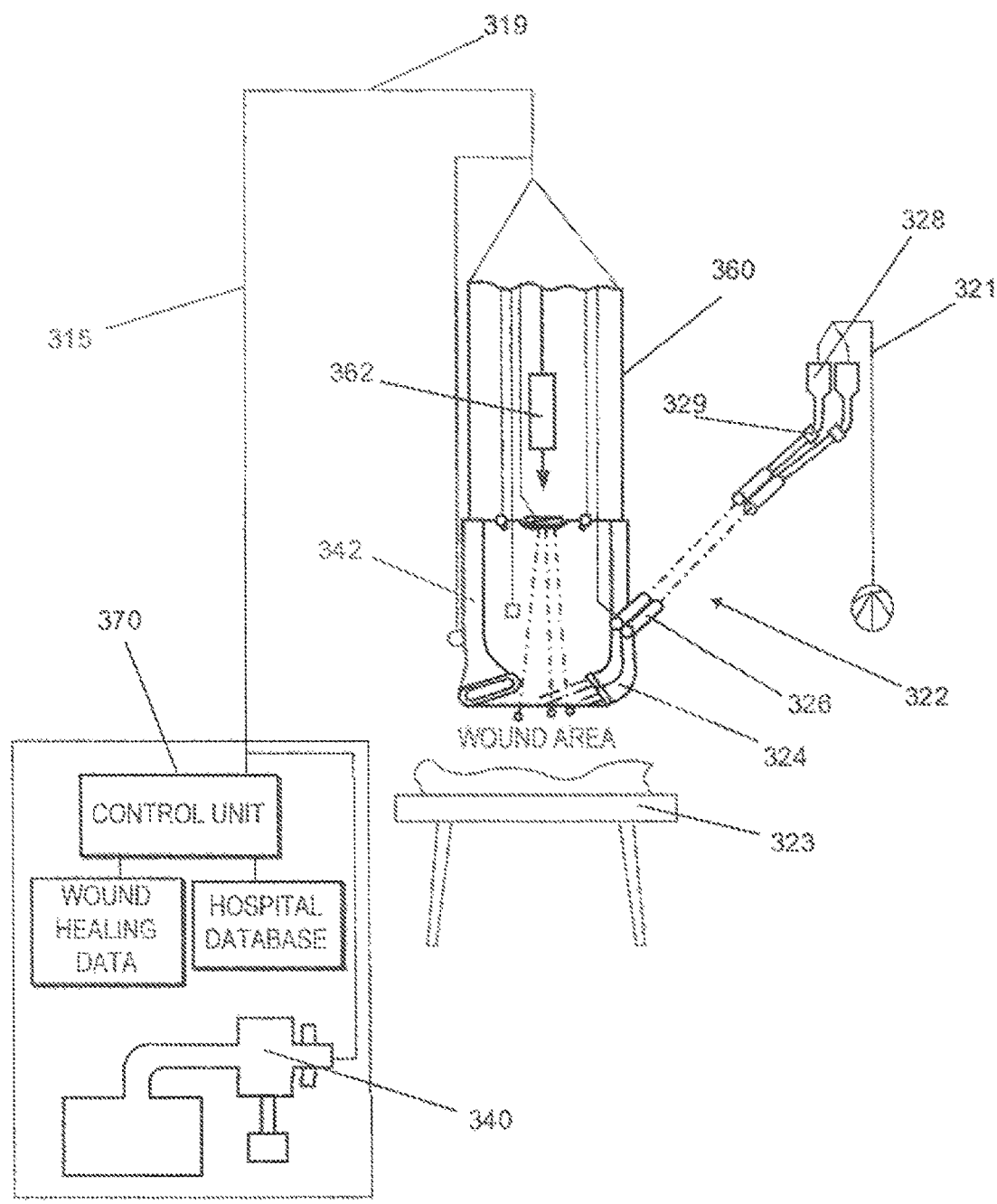
FIG. 10 is a schematic diagram illustrating operation of the system of the invention.
Figure 11:
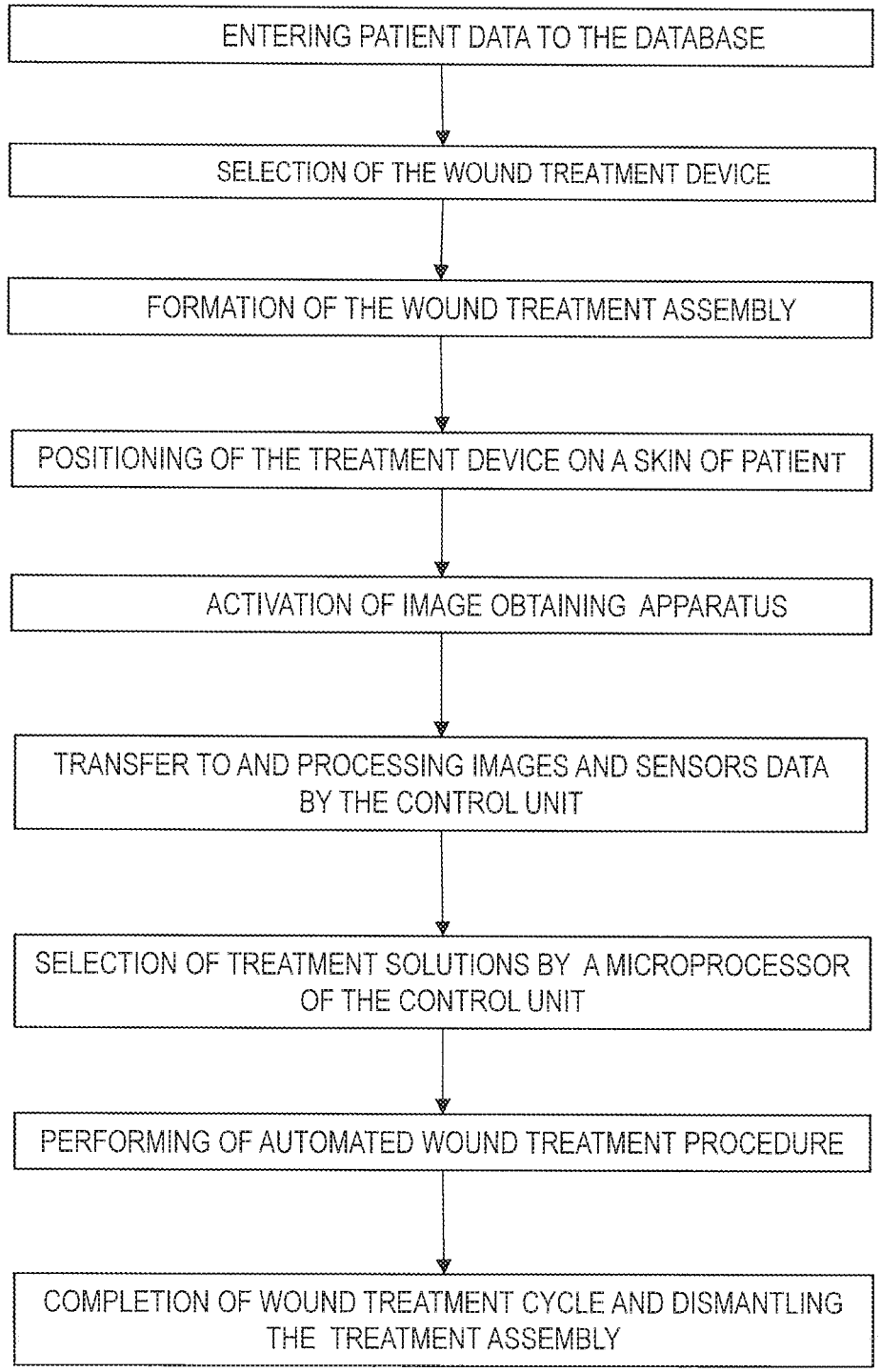
FIG. 11 is a process flow diagram showing a method for treatment of wounds and skin medical conditions at a predetermined skin area.

Referring now to FIG. 10 showing the treatment assembly 300 mounted to an external mechanical apparatus e.g., tripod, or movable stand 315 with a pivoting arm 319 allowing convenient use of the device by an operator or mobility of the device within a clinical room with hands-free operation of the device. The treatment assembly consists of a treatment device with a housing 310 releasably engaging to the handheld device 360 containing a laser source or emitter, an image recording device, a scanner, multiple sensors and a control unit. The housing having the suction outlet 342 is connected to the system 340 for evacuation of the necrotic tissue and spent liquids also supported by the movable stand.

As to the fluid delivery mechanism 322, the nozzles 324 connected to the pumps 326 are associated with the housing. On the other hand, the multiple storages/containers 328 with the medical debridement liquids/fluids and the cooling arrangements 329 are supported by the independent ivy stand 321. In use a patient is positioned on the treatment table 323 with a wound being exposed for the treatment. Through a connecting pipeline the storage containers supported by the ivy stand 321 are connected the pumps 326 and the fluid delivery mechanism is activated by the control unit algorithm.

As to the fluid delivery mechanism 322, the multiple storages/containers 328 with the medical debridement liquids/fluids, the pumps 326 and the cooling arrangements 329 are separate from the housing 310 and supported by the independent ivy stand 321. Through a connecting pipeline the fluid delivery mechanism 322 located on the ivy stand 321 is connected to the nozzles 324 of the housing 310.

Referring now to FIG. 111 which is a process flow diagram showing a method for treatment of wounds and skin medical conditions at a predetermined skin area of the invention utilizing the treatment assembly, the method comprises of the following steps: Entering patient identifier data into a wound healing data base to access the memory containing prior patient history/if any.

The treatment device is selected to accommodate specific wound characteristics, including size, shape, intensity, etc. for optimal treatment of a specific wound at a predetermined skin area.

A wound treatment assembly is formed by connection of the selected treatment device or treatment vessel to the source or containers with wound treatment medications and solutions. The top region of the treatment housing is securely, but releasably fastened to the connecting area of the laser handpiece and the components situated in the handpiece such as the laser, scanning device, video camera, sensors, etc. are checked.

Then, the treatment device or vessel of the wound treatment assembly is positioned by an operator on a skin of a patient surrounding the wound. In the embodiment of the treatment device illustrated in FIGS. 8 and 9, which are formed with the isolation vacuum arrangement, the auxiliary pump is activated to create a vacuum in the space between the double walls, so as to secure and isolate the skin surrounding the wound from outside influence and to prevent the medications and/or treatment debris to contaminate outside of the treatment area.

The image generating device or camera in the handpiece is activated and images or photographs of the wound are taken in either regular light and/or specially selected mono chromatic light or other optimal illumination; wherein other sensors record various characteristic of the wound, such as temperature, color for example.

Data generated by the camera and sensors is transferred to the microprocessor of the control unit where the data is compared to the prior patient data stored in the memory (if available), and calculation of the laser parameters utilized during the wound treatment procedure is conducted.

The algorithm of the microprocessor selects required/predetermined medicative solution for delivery to the wound disposed in the treatment chamber, if needed oxygen is fed for mixing with solution producing suspension applied during the treatment.

An operator initiates automatic wound treatment procedure which is performed according to the treatment protocol individually tailored to the condition of the specific wound of a patient. The necrotic tissue and spent suspension/solution are removed from the treatment chamber by suction generated by the evacuation system to further promote wound healing.

Upon completion of the wound treatment cycle, the treatment assembly is dismantled, so that the treatment device being detached from the handpiece, and the medication pumps and the negative pressure pump being disconnected.

Upon completion of the wound treatment cycle, the treatment chamber of the (disposable) vessel s vacuumed to dispose the wound debris and wound treatment solutions and then dried by the air stream forced through the internal cavity by the negative pressure (suction) while the housing continue to be attached and sealed to the wound area. The condition of the treated wound is again photographed, other characteristics recorded by sensors. The data send to the patient data base. As the final step the negative pressure/suction under the device is released and removed from the skin surrounding the wound.

The above method is different in many respects from the current practice, wherein wounds are manually treated by medical personnel using gauze and scalpel. It is true that certain suspension containing oxygen are currently used for washing the wounds, however the minimally invasive comprehensive protocol for wound treatment combining minimally invasive use of laser energy for debridement and collagen proliferation together with individually tailored based on objective readings for current wound condition application of solution based medications as discussed above is not currently known.

What is claimed is:

1. A system for treatment of wounds and skin medical conditions, comprising:

a control unit, a handheld device and a predetermined disposable kit, the handheld device and the disposable kit being separate and distinct;

the disposable kit comprising: a disposable treatment vessel selected for treatment of predetermined wound characteristics of a patient, the disposable treatment vessel having a housing defined by a peripheral wall extending between a top region and an open bottom region to be situated at a wound treatment area, a treatment chamber formed in an interior of the housing, a liquid delivery mechanism for supplying predetermined debridement liquids to the wound treatment area having at least one dispensing nozzle situated at the bottom region of the treatment chamber of the disposable treatment housing, and an evacuation mechanism for evacuation of debris from the treatment chamber having at least one suction outlet at the bottom region of the disposable treatment housing;

the handheld device releasably connected to the top region of the disposable kit treatment housing at a connecting area forming an interface between the handpiece and the top region, an interior of the handheld device having a laser source, a laser beam scanning device, an image recording apparatus and at least one sensor provided within the handheld device at said interface;

the control unit with a microprocessor having an algorithm stored thereon for controlling operation of the system, the control unit provided outside of the handheld device;

wherein said at least one sensor detects and measures concentration of various substances in the wound, said microprocessor receives and analyzes data obtained by said at least one sensor and generates signals to adjust parameters of the laser, the at least one dispensing nozzle and the suction outlet to optimize removal of necrotic tissue at the bottom region of the disposable kit treatment housing to promote the wound area healing;

the algorithm of the microprocessor utilizes wound images generated by the image recording apparatus to define the wound treatment area by a laser beam and guide the laser beam scanning device to thoroughly cover the wound treatment area in an optimal pattern; and wherein said disposable kit including said predetermined debridement liquids are selected to accommodate the predetermined wound characteristics of a selected skin area before being connected to the handheld device, so that each patient is provided with personalized disposable treatment vessel accommodating treatment of specific wound characteristics.

2. The system of claim 1, wherein said liquid delivery mechanism of said disposable kit further comprises an external portion situated outside of the treatment chamber peripheral wall, the external portion comprises at least one pump, and multiple containers having predetermined types of the wound treatment liquids.

3. The system of claim 2, wherein said at least one dispensing nozzle of said disposable kit comprises multiple nozzles provided at different elevations in the treatment chamber.

4. The system of claim 2, wherein said liquid delivery mechanism of said disposable kit further comprises a cooling arrangement provided between the containers and the pump for cooling the predetermined debridement liquids prior to delivery to the treatment chamber of said disposable kit through the peripheral wall.

5. The system of claim 1, wherein said evacuation mechanism of said disposable kit further comprises at least one pump situated outside of the treatment chamber peripheral wall connected to the at least one suction outlet to create a low-pressure zone in the treatment chamber, a debris storage container and a filter situated outside of the treatment chamber upstream of system for aspirated tissue material evacuation suction system.

6. The system of claim 5, wherein said at least one pump is connected to a pulse modulator forming pressure differentials in the evacuation system, so that the pulse modulator creates pulses of suction pressure within said disposable kit treatment chamber.

7. The system of claim 1, wherein said at least one sensor emits and receives more than one signals selected from the group consisting of optical, electromagnetic, acoustical and capacitance measuring signals, said more than one signals passing through said interface into said disposable kit treatment chamber.

8. The system of claim 1, wherein said at least one sensor comprises multiple sensors, application of the debridement liquids to the wound treatment area is controlled by said algorithm based on review of pictorial data of the material accumulated at the bottom region of said disposable kit treatment chamber produced by the imaging recording apparatus and the sensors situated in the hand held device at said interface.

9. The system of claim 8, wherein said sensors detect and measure concentration of various characteristics in the wound treatment area, said characteristics are selected from the group comprising hemoglobin, melanin, water, different bacteria and materials produced by said bacteria.

10. The system of claim 1, further comprising at least one thermal detector situated within the said disposable kit treatment treatment chamber, wherein operation of the control unit is adjusted based on inputs from said at least one sensor, said at least one thermal detector and video images generated by the image recording apparatus based on a pictorial data of the material accumulated at the bottom region of the said disposable kit treatment chamber.

11. The system of claim 1, wherein said microprocessor receives and analyzes data obtained by said at least one sensor and generates signals passing through said handheld device into said disposable kit treatment chamber to adjust characteristics of said laser source, said at least one liquid dispensing nozzle and said at least one suction outlet to optimize the debridement of necrotic tissue accumulated at the bottom region of the said disposable kit treatment chamber and treatment of the wound area.

12. The system of claim 1, wherein said image recording apparatus is a digital camera having wireless data transfer capabilities, said camera is operable at different wavelengths supporting illumination function, said digital camera allows the control unit including the microprocessor, by highlighting the wound treatment area at certain wavelengths, to determine a presence of chemical or biological substances in the wound area and a respective surrounding skin tissue.

13. The system of claim 1, wherein said at least one sensor generates signals directed to the control unit to facilitate measuring hemoglobin concentration in the wound area, temperature detector provides data to the control unit to optimally control an amount of laser energy applied to the wound area and is used to control an energy in the pulse, pattern and repetition rate of laser pulse application to the wound area.

14. The system of claim 1, wherein the top region of said disposable kit being translucent to a laser and other types of radiation.

15. The system of claim 1, wherein said disposable kit treatment housing is formed with multiple ports integrated into the peripheral wall that allow creation of a negative pressure zone in the treatment chamber near the wound treatment area.

16. A method of treatment of wounds and skin medical conditions utilizing the system of claim 1, comprising: providing the system of claim 1; and selecting said disposable kit including selecting said predetermined debridement liquids before said disposable kit being connected to the handheld device, to accommodate the predetermined wound characteristics of a selected skin area.

17. A method of treatment wounds and skin medical conditions utilizing the system of claim 1, comprising: a step of connecting the external portion of the said disposable kit fluid delivery mechanism to said at least one dispensing nozzle before said system is activated.

* * * * *